United States Patent
Evans et al.

(10) Patent No.: US 10,687,811 B2
(45) Date of Patent: Jun. 23, 2020

(54) SURGICAL INSTRUMENTS INCLUDING SENSORS

(71) Applicant: Covidien LP, Mansfield, MA (US)

(72) Inventors: Christopher K. Evans, Southington, CT (US); Matthew Eschbach, Cheshire, CT (US)

(73) Assignee: Covidien LP, Mansfield, MA (US)

( * ) Notice: Subject to any disclaimer, the term of this patent is extended or adjusted under 35 U.S.C. 154(b) by 316 days.

(21) Appl. No.: 15/453,241

(22) Filed: Mar. 8, 2017

(65) Prior Publication Data

US 2018/0256163 A1     Sep. 13, 2018

(51) Int. Cl.
| | |
|---|---|
| *A61B 17/072* | (2006.01) |
| *A61B 17/068* | (2006.01) |
| *A61B 5/026* | (2006.01) |
| A61B 17/00 | (2006.01) |
| A61B 17/28 | (2006.01) |
| A61B 17/29 | (2006.01) |
| A61B 90/00 | (2016.01) |

(52) U.S. Cl.
CPC ...... *A61B 17/07207* (2013.01); *A61B 5/0261* (2013.01); *A61B 17/068* (2013.01); *A61B 2017/00022* (2013.01); *A61B 2017/0046* (2013.01); *A61B 2017/00115* (2013.01); *A61B 2017/00199* (2013.01); *A61B 2017/00221* (2013.01); *A61B 2017/00473* (2013.01); *A61B 2017/00557* (2013.01); *A61B 2017/07257* (2013.01); *A61B 2017/07271* (2013.01); *A61B 2017/2825* (2013.01); *A61B 2017/2926* (2013.01); *A61B 2090/065* (2016.02); *A61B 2562/0247* (2013.01)

(58) Field of Classification Search
None
See application file for complete search history.

(56) References Cited

U.S. PATENT DOCUMENTS

| | | |
|---|---|---|
| 4,109,647 A | 8/1978 | Stern et al. |
| 4,862,894 A | 9/1989 | Fujii |

(Continued)

FOREIGN PATENT DOCUMENTS

| | | |
|---|---|---|
| EP | 2573190 A1 | 3/2013 |
| EP | 2742873 A1 | 6/2014 |

(Continued)

OTHER PUBLICATIONS

European Search Report dated Jul. 21, 2015, issued in European Application No. 14 19 9657.

(Continued)

*Primary Examiner* — Hemant Desai
*Assistant Examiner* — Tanzim Imam
(74) *Attorney, Agent, or Firm* — Carter, DeLuca & Farrell LLP

(57) ABSTRACT

A surgical instrument includes a handle portion, a shaft coupled to the handle portion, a pair of jaw members operably coupled to the shaft, an inflatable member, and a sensor. The inflatable member is associated with one of the jaw members and is configured to apply pressure to tissue disposed between the pair of jaw members. The sensor is associated with one of the jaw members and is configured to measure local perfusion pressure in the tissue disposed between the pair of jaw members.

14 Claims, 11 Drawing Sheets

(56) References Cited

U.S. PATENT DOCUMENTS

| | | | |
|---|---|---|---|
| 5,395,033 A | 3/1995 | Byrne et al. | |
| 5,518,164 A | 5/1996 | Hooven | |
| 5,722,419 A | 3/1998 | Semmlow et al. | |
| 5,769,791 A | 6/1998 | Benaron et al. | |
| 7,172,104 B2 | 2/2007 | Scirica et al. | |
| 7,223,279 B2 | 5/2007 | Burbank et al. | |
| 7,229,465 B2 | 6/2007 | Burbank et al. | |
| 7,618,376 B2 | 11/2009 | Kimball | |
| 8,002,795 B2 | 8/2011 | Beetel | |
| 8,073,518 B2 | 12/2011 | Chin | |
| 8,118,206 B2 | 2/2012 | Zand et al. | |
| 8,157,145 B2 | 4/2012 | Shelton, IV et al. | |
| 8,684,250 B2 * | 4/2014 | Bettuchi | A61B 17/072 227/179.1 |
| 8,808,311 B2 | 8/2014 | Heinrich et al. | |
| 9,204,830 B2 | 12/2015 | Zand et al. | |
| 2003/0120306 A1 | 6/2003 | Burbank et al. | |
| 2004/0127800 A1 | 7/2004 | Kimball et al. | |
| 2005/0101974 A1 | 5/2005 | Burbank et al. | |
| 2005/0131390 A1 | 6/2005 | Heinrich et al. | |
| 2006/0122462 A1 * | 6/2006 | Roth | A61B 17/0218 600/204 |
| 2006/0235314 A1 | 10/2006 | Migliuolo et al. | |
| 2009/0234248 A1 | 9/2009 | Zand et al. | |
| 2011/0144640 A1 | 6/2011 | Heinrich et al. | |
| 2011/0290851 A1 * | 12/2011 | Shelton, IV | A61B 17/07207 227/176.1 |
| 2012/0116185 A1 | 5/2012 | Zand et al. | |
| 2013/0030262 A1 * | 1/2013 | Burnett | A61B 5/0215 600/309 |
| 2014/0107697 A1 | 4/2014 | Patani et al. | |
| 2014/0121508 A1 * | 5/2014 | Latimer | A61B 5/4848 600/427 |
| 2014/0135604 A1 | 5/2014 | Cuesta Valentin et al. | |
| 2014/0148751 A1 | 5/2014 | Kassab et al. | |
| 2014/0288386 A1 | 9/2014 | Zand et al. | |
| 2014/0343375 A1 * | 11/2014 | Mannheimer | A61B 5/14551 600/301 |
| 2015/0173789 A1 * | 6/2015 | Baxter, III | A61B 17/07207 606/130 |
| 2016/0118201 A1 | 4/2016 | Nicholas et al. | |
| 2016/0296227 A1 * | 10/2016 | Gleiman | A61B 17/1155 |
| 2018/0014826 A1 * | 1/2018 | Scheib | A61B 17/00234 |
| 2018/0103861 A1 * | 4/2018 | Sutin | A61B 5/6814 |

FOREIGN PATENT DOCUMENTS

| | | | | |
|---|---|---|---|---|
| TW | 201409026 A | 3/2014 | | |
| WO | 03/101277 A2 | 12/2003 | | |
| WO | 2006113394 A2 | 10/2006 | | |
| WO | 2007008057 A1 | 1/2007 | | |
| WO | 2008085025 A1 | 7/2008 | | |
| WO | WO-2008085025 A1 * | 7/2008 | | A61B 17/29 |
| WO | WO-2015057533 A1 * | 4/2015 | | A61B 8/12 |
| WO | WO-2016164891 A1 * | 10/2016 | | A61B 5/0476 |

OTHER PUBLICATIONS

European Office Action corresponding to counterpart Int'l Appln. No. EP 14 19 9657.9 dated Jul. 9, 2016.

European Search Report dated Jul. 12, 2018, corresponding to European Application No. 18160402.6; 7 pages.

European Extended Search Report dated Nov. 23, 2018, corresponding to European Application No. 18180392.5; 10 pages.

* cited by examiner

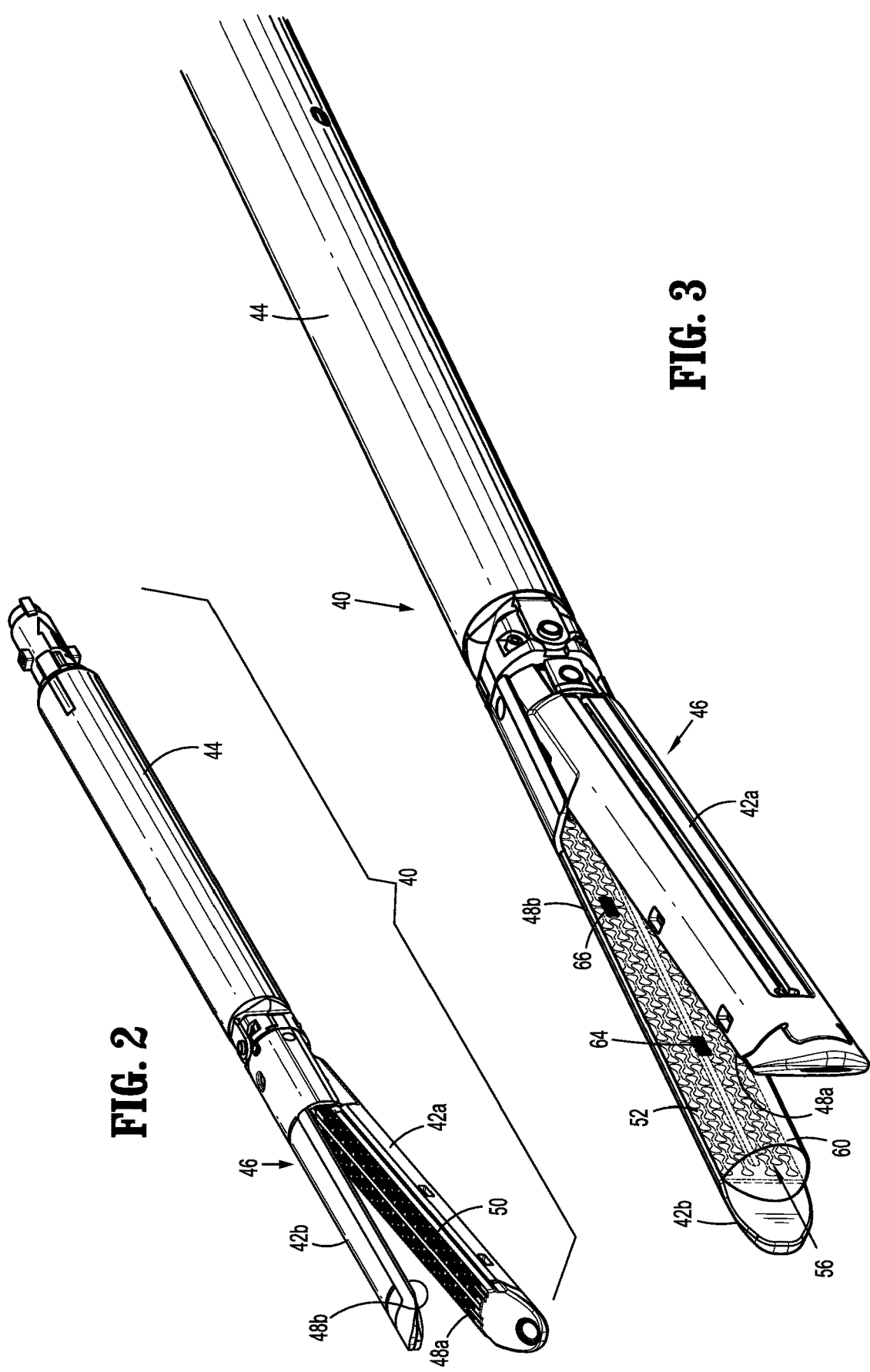

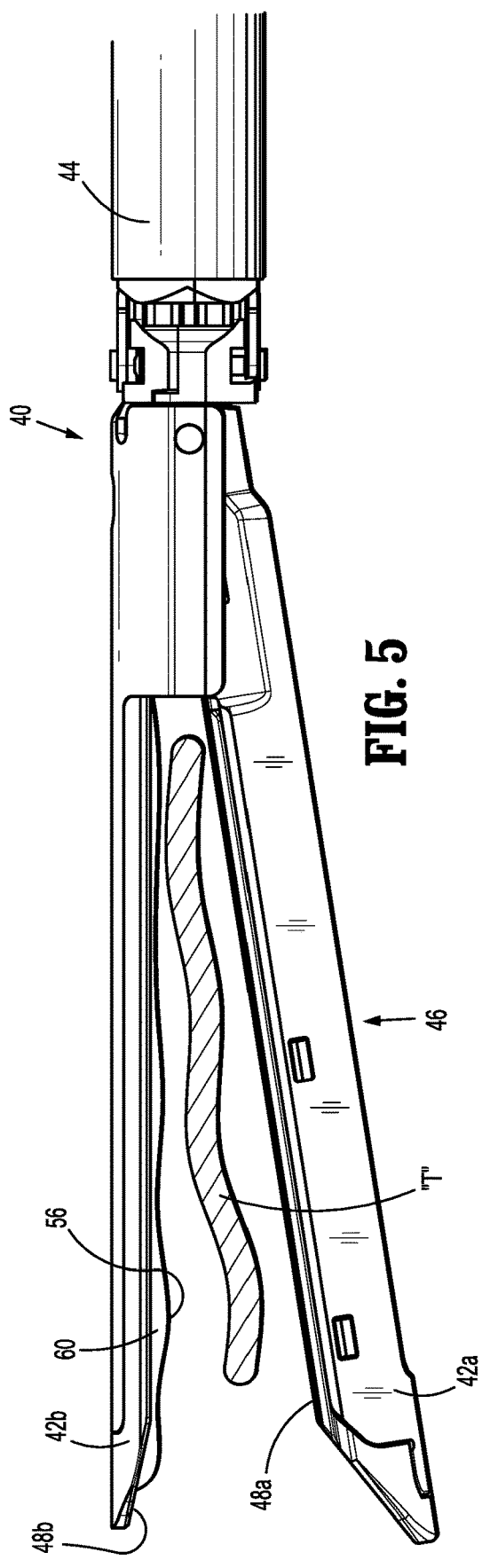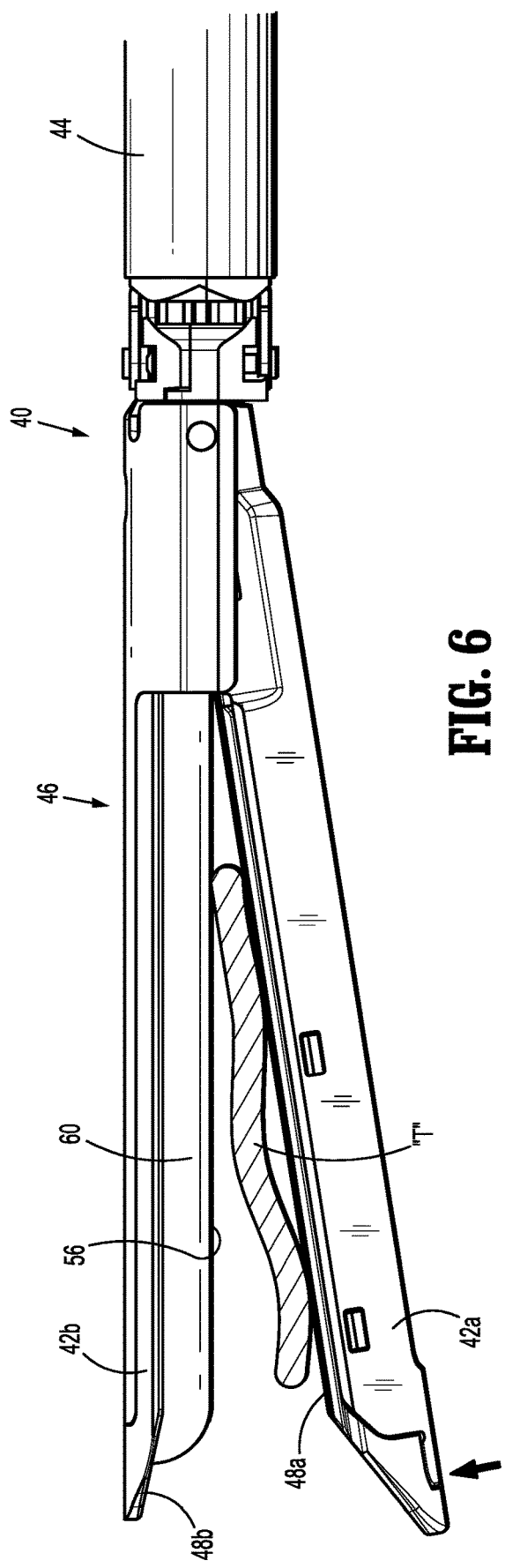

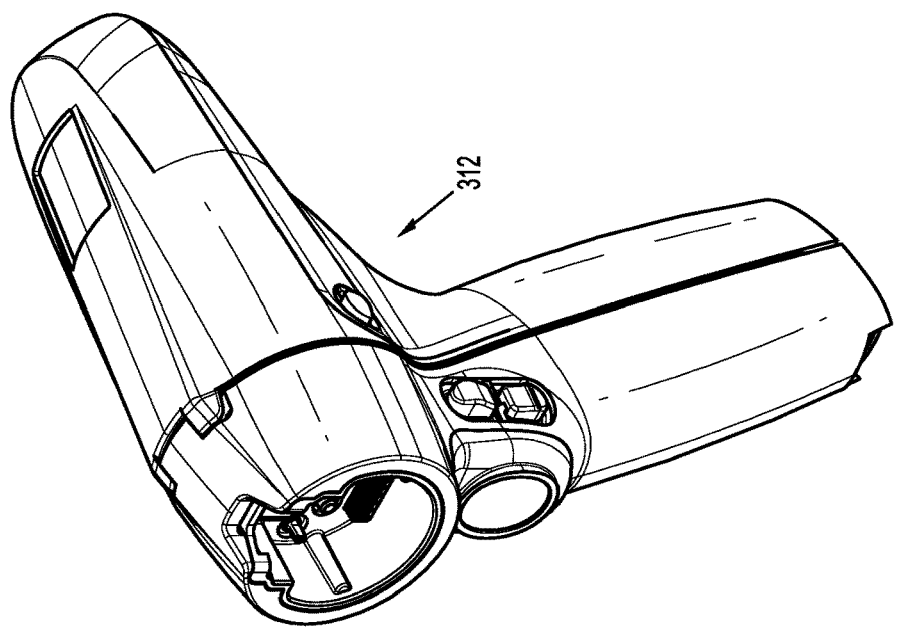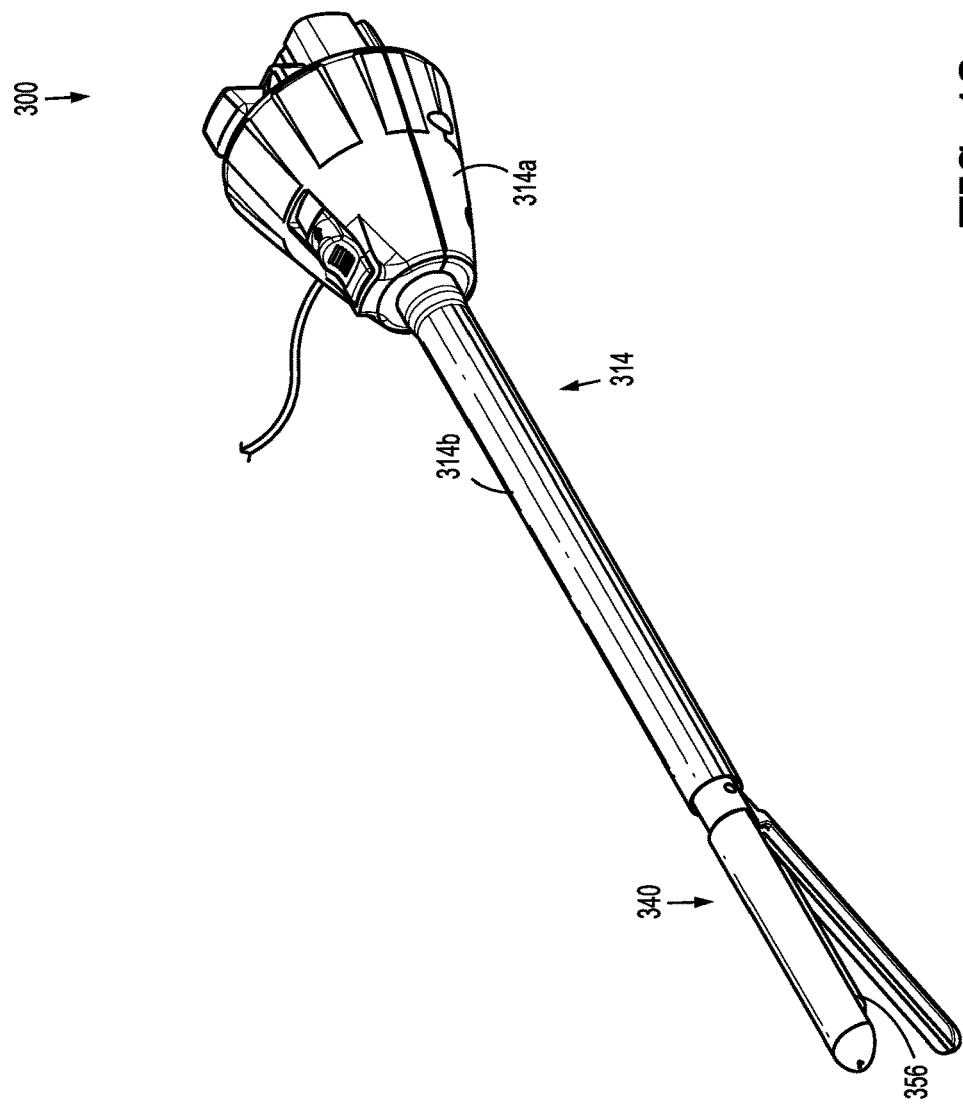
FIG. 13

SURGICAL INSTRUMENTS INCLUDING SENSORS

BACKGROUND

1. Technical Field

The present disclosure relates to surgical instruments and, more particularly, to surgical instruments for grasping tissue and determining characteristics of the grasped tissue in preparation for performing various surgical procedures.

2. Background of Related Art

Surgical procedures sometimes involve the cutting and closure of tissue. For example, colorectal surgery sometimes requires anastomosis, which involves resecting a piece of diseased bowel tissue and creating a new connection between presumably two healthy bowel segments. Typically, before performing the anastomosis, the amount of tissue to be resected is estimated using visual indicia of the bowel. A goal of performing the anastomosis is to preserve as much healthy tissue as possible while at the same time removing all of the diseased tissue.

A risk involved in performing an anastomotic procedure is anastomotic leaks. The anastomotic leaks are typically caused by a failure to resect all of the diseased tissue. Current methods used in estimating the amount of tissue to be resected during an anastomotic procedure are sometimes inadequate in preventing all anastomotic leaks.

Accordingly, a need exists for surgical instruments that can sense, either sequentially or simultaneously, one or more parameters of the bowel tissue to aid a clinician in performing a more successful anastomotic surgical procedure.

SUMMARY

In one aspect of the present disclosure, a surgical instrument is provided and includes a handle portion, a shaft coupled to the handle portion, a pair of jaw members operably coupled to the shaft, an inflatable member, and a first sensor. The jaw members are movable relative to one another between spaced and approximated positions in response to an actuation of the handle portion. The inflatable member is associated with one of the jaw members and is configured to apply pressure to tissue disposed between the pair of jaw members. The first sensor is associated one of the jaw members and is configured to measure local perfusion pressure in the tissue disposed between the jaw members.

In some embodiments, the surgical instrument may further include a second sensor in communication with the inflatable member. The second sensor is configured to measure a pressure within the inflatable member.

In some embodiments, one of the jaw members may include a tissue-contacting surface on which the inflatable member is disposed. The inflatable member is clamped between the jaw members when the jaw members are in the approximated position.

In some embodiments, the inflatable member may be disposed within a cavity defined in one of the jaw members.

In some embodiments, the jaw members may be configured to staple tissue disposed therebetween.

In some embodiments, a first jaw member may include a tissue-contacting surface that defines staple-forming pockets, and a second jaw member may include a tissue-contacting surface that defines staple-receiving channels.

In some embodiments, the inflatable member may be a balloon fabricated from an elastomer.

In some embodiments, the inflatable member may have a tube configured to be in fluid communication with a pump for inflating the inflatable member.

In some embodiments, the inflatable member may be configured to transition between a collapsed state, in which the inflatable member is substantially flat, and an expanded state, in which the inflatable member is bulbous.

In some embodiments, the inflatable member may define a hollow inner chamber therein.

In some embodiments, the handle portion may include a manual trigger for effecting a closing of the pair of jaw members.

In some embodiments, the handle portion may be configured to effect a closing of the pair of jaw members via an internal power source.

In some embodiments, the surgical instrument may further include an adapter assembly interposed between the handle portion and the shaft.

In another aspect of the present disclosure, a surgical loading unit is provided and includes an elongate body and an end effector coupled to a distal portion of the elongate body. The end effector includes a pair of jaw members, an inflatable member, and a first sensor. The jaw members are movable relative to one another between spaced and approximated positions. The inflatable member is associated with one of the jaw members and is configured to apply pressure to tissue disposed between the jaw members. The first sensor is associated with one of the jaw members and is configured to measure local perfusion pressure in the tissue disposed between the jaw members.

In another aspect of the present disclosure, a method of performing a surgical procedure is provided and includes positioning tissue between a pair of jaw members of a surgical instrument. An inflatable member associated with one of the jaw members is inflated, thereby applying pressure on the tissue with the inflatable member. Local perfusion pressure of the tissue is measured using a perfusion sensor associated with one of the jaw members. It is determined whether the tissue is in condition for stapling using the measured local perfusion pressure of the tissue.

These and other objects will be more clearly illustrated below by the description of the drawings and the detailed description of the preferred embodiments.

BRIEF DESCRIPTION OF THE DRAWINGS

The accompanying drawings, which are incorporated in and constitute a part of this specification, illustrate embodiments of the present disclosure and, together with the detailed description of the embodiments given below, serve to explain the principles of the disclosure.

FIG. 2 is a front, perspective view of a surgical loading unit of the surgical instrument of FIG. 1;

FIG. 3 is an enlarged perspective view of the surgical loading unit of FIG. 2 illustrating an inflatable member of the surgical loading unit in an inflated state;

FIG. 5 is a partial, side view of the surgical loading unit of FIG. 3 illustrating tissue disposed between jaw members of the surgical loading unit with the inflatable member in a collapsed state and the jaw members in a partially open position;

FIG. 6 is a partial, side view of the surgical loading unit of FIG. 3 illustrating tissue disposed between the jaw members with the inflatable member in an expanded state and the jaw members in the partially open position;

FIG. 13 is a perspective view, with parts separated, of a handle portion and an adapter assembly/jaw assembly of the surgical instrument of FIG. 12.

DETAILED DESCRIPTION

Figure 1:
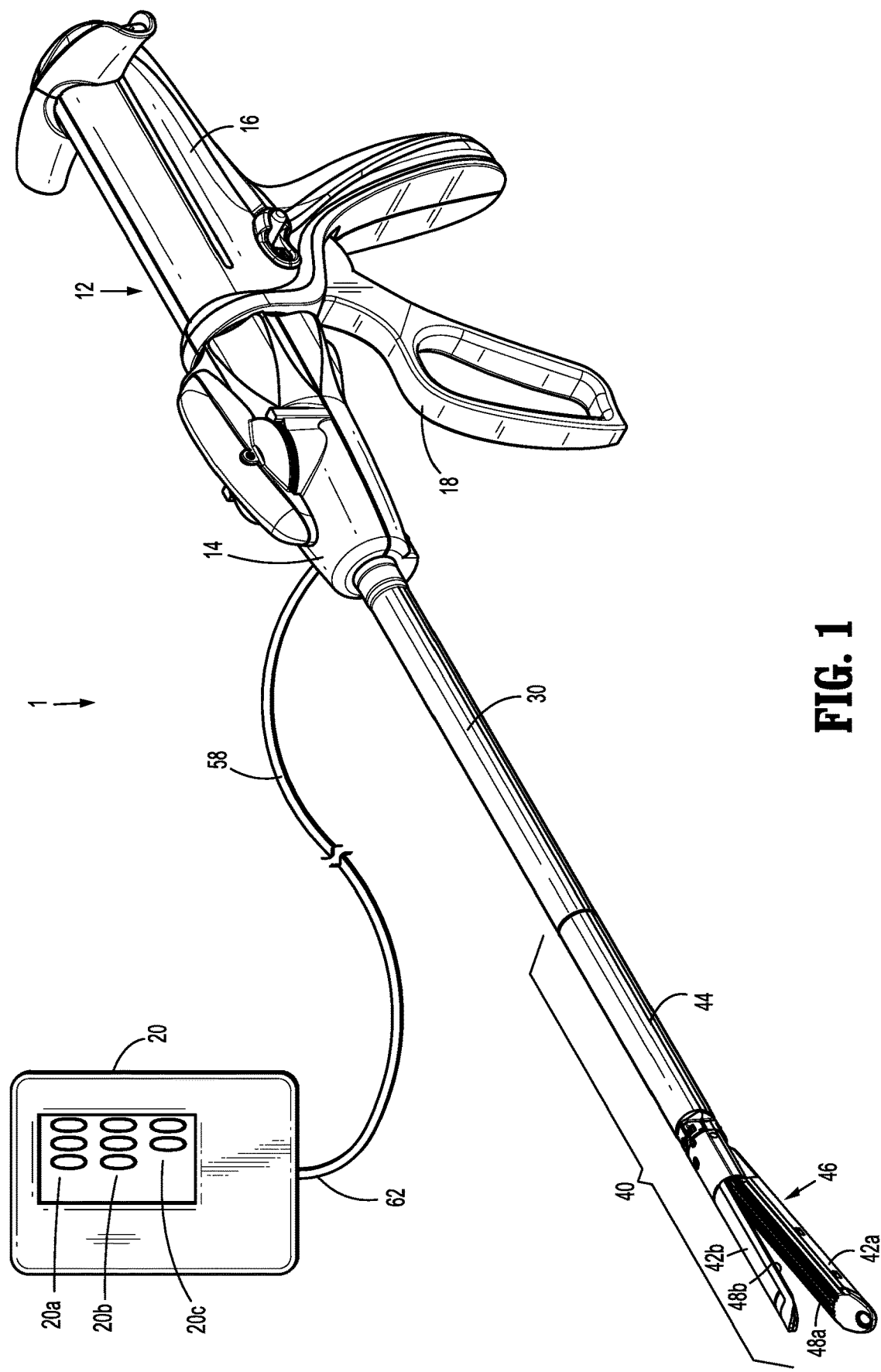
FIG. 1 is a perspective view of one embodiment of a surgical system including a display and a surgical instrument.

Embodiments of the presently disclosed surgical instruments and systems will now be described in detail with reference to the drawing figures wherein like reference numerals identify similar or identical elements. As used herein and as is traditional, the term "distal" will refer to that portion which is further from the user while the term "proximal" will refer to that portion which is closer to the user.

FIG. 1 illustrates a surgical system 1 which generally includes a surgical instrument such as a surgical stapler 10 in communication with a display 20 for displaying measurements taken by the surgical stapler 10. The surgical stapler 10 is configured to staple grasped tissue and to sense biological parameters of the tissue to assist a clinician in determining whether to effect a stapling function of the surgical stapler 10, as will be described in detail herein. For example, the surgical stapler 10 is configured to determine a surface perfusion pressure of a subject tissue. In embodiments, the surgical stapler 10 is configured for use in laparoscopic surgical procedures. The surgical stapler can be arranged for use in a robotic surgical system.

The surface perfusion pressure of tissue is measured by applying clamping pressure on the tissue until there is no perfusion (i.e., no blood flow) through the tissue, and then slowly reducing the clamping pressure until perfusion through the grasped tissue restarts. The pressure at which the perfusion restarts is known as "surface perfusion pressure."

For a detailed description of a method of measuring surface perfusion pressure, reference may be made to U.S. Pat. No. 7,618,376, the entire contents of which are incorporated by reference herein.

The surgical stapler 10 generally includes a handle portion 12, an adapter assembly 14, an elongated shaft 30, and a surgical loading unit 40. The handle portion 12 of the surgical stapler 10 includes a stationary handle 16 and a pivoting or movable handle 18 pivotably coupled to the stationary handle 16. Manipulation of the pivoting handle 18 relative to the stationary handle 16 effects a closing of jaw members 42a, 42b of the surgical loading unit 40 to grasp tissue disposed between the jaw members 42a, 42b. For a detailed description of the various functions of the surgical stapler 10, reference may be made to, for example, U.S. Pat. No. 7,172,104, the entire contents of which are incorporated by reference herein.

The surgical loading unit 40 has an elongate body portion 44 and an end effector 46 coupled to the body portion 44. The body portion 44 is detachably coupled to a distal portion of the elongated shaft 30 or, in some embodiments, may be fixedly coupled to the distal portion of the elongated shaft 30. The end effector 46 of the surgical loading unit 40 is pivotably coupled to a distal portion of the body portion 44 such that the end effector 46 may be articulated about an axis transverse to a longitudinal axis of the body portion 44 between a linear orientation and an angled orientation relative to the longitudinal axis. In some embodiments, the end effector 46 may be fixedly attached to the distal portion of the elongated shaft 30.

With reference to FIGS. 1-3, the end effector 46 includes a pair of opposing jaw members 42a, 42b, wherein the jaw member 42a is configured as a staple cartridge and the jaw member 42b is configured as an anvil. The staple cartridge 42a and the anvil 42b each define a respective tissue-contacting surface 48a, 48b. The tissue-contacting surfaces 48a, 48b oppose one another such that when the end effector 46 is in the closed configuration, tissue is grasped between the tissue contacting surfaces 48a, 48b. The tissue-contacting surface 48a of the staple cartridge 42a defines a plurality of staple-receiving channels 50, and the tissue-contacting surface 48b of the anvil 42b defines a plurality of staple forming pockets 52. As such, the staple cartridge 42a and the anvil 42b are configured to clamp and then staple tissue disposed therebetween in response to an actuation of the movable handle of the handle portion 12.

The end effector 46 of the surgical loading unit 40 includes an inflatable member 56 (FIG. 3), such as, for example, a balloon, disposed on the tissue-contacting surface 48b of the anvil 42b. In other embodiments, the inflatable member 46 may be disposed on the tissue-contacting surface 48a of the staple cartridge 42a. In still other embodiments, each of the staple cartridge 42a and the anvil 42b may have an inflatable member disposed on its respective tissue-contacting surface 48a, 48b. The inflatable member 56 may be attached to the tissue-contacting surface 48b via an adhesive, a hook and loop fastener, a suture, or the like. In some embodiments, the inflatable member 56 may be detachably connected to the tissue-contacting surface 48b. In other embodiments, the inflatable member 56 may be detachably connected to the tissue-contacting surface 48b such that upon an actuation of the stapling function of the end effector 46, the staples ejected from the staple cartridge 42a release the inflatable member 56 from the tissue-contacting surface 48b, for example, by severing a suture that attaches the inflatable member 56 to the tissue-contacting surface 48b.

The inflatable member 56 has a generally rectangular shape dimensioned to cover the tissue-contacting surface 48b of the anvil 42b such that the staple forming pockets 52 defined in tissue-contacting surface 48b are covered by the inflatable member 56. The inflatable member 56 is fabricated from a biocompatible material such as natural or synthetic elastomers, natural or synthetic rubbers and silicone materials, and/or compliant polyurethanes. The inflatable member 56 may be made of a material that is penetrable by the staples ejected from the staple cartridge 42a so as to not inhibit the stapling function of the end effector 46.

The inflatable member 56 defines a hollow inner chamber or void 60 that receives a fluid to change or move the inflatable member 56 from a collapsed configuration, in which the inflatable member 56 is substantially flat and rectangular (FIG. 5), to an expanded configuration, in which the inflatable member 56 is larger than in the collapsed configuration and assumes a bulbous configuration (FIG. 6). In some embodiments, the inflatable member 56 may be configured to assume any suitable shape when in the expanded configuration, such as, for example, rectangular, dome-shaped, elliptical, oblong, tubular, square, triangular, cylindrical, rod-shaped, or the like.

The inflatable member 56 may have a hose or tube 58 (FIG. 1) extending therefrom and in fluid communication with the hollow inner chamber 60 (FIG. 3). The tube 58 may extend from the inflatable member 56, proximally through the body portion 44 of the surgical loading unit 40, the elongated shaft 30, and out of the adapter assembly 14. The tube 58 may have an end 62 (FIG. 1) coupled to a source of fluid, such as, for example, a pump (not explicitly shown), for delivering a fluid, such as liquid and/or gas, into the hollow inner chamber 60 (FIG. 3) of the inflatable member 56. The end 62 of tube 58 may be in communication with the display 20 (FIG. 1) or a processor of the display 20.

The end effector 46 of the surgical loading unit 40 includes a first sensor 64 (FIG. 3) and a second sensor 66 (FIG. 3) each associated with the anvil 42b. In particular, the first and second sensors 64, 66 are each attached to the inflatable member 56 of the anvil 42b and in communication with the display 20. In some embodiments, the first sensor 64 may be attached to one or both of the tissue-contacting surfaces 48a, 48b of the respective staple cartridge 42a and anvil 42b. The first sensor 64 is a perfusion sensor, for example, a Doppler flow sensor, configured to measure local perfusion (i.e., blood flow) through tissue grasped between the staple cartridge 42a and the anvil 42b. The first sensor 64 may measure perfusion of the grasped tissue on the basis of known techniques, such as Laser-Doppler Flowmetry ("LDF"), measuring light scattering, and/or measuring absorption of light from one or more LED's or other light sources. For a detailed description of LDF technology, reference may be made to U.S. Pat. Nos. 4,109,647 and 4,862,894, the entire contents of each of which are incorporated by reference herein.

The first sensor 64 is in communication, via lead wires or wireless connection, with the display 20 such that upon the first sensor 64 measuring perfusion in grasped tissue, the first sensor 64 transmits the measurement data to a first display section 20a of the display 20, which displays the measurement using a number, word, or image. In some embodiments, the first sensor 64 may also be in communication, via lead wires or wireless connection, with a computing device or processor (not shown) such as a laser Doppler monitor, which processes the information collected by the first sensor 64 to calculate the tissue perfusion. The computing device (e.g., a laser Doppler monitor) may also be in communication, via lead wires or wireless connection, with the first display section 20a to send the processed information related to the tissue perfusion to the first display section 20a so that the first display section 20a can display the tissue perfusion.

The second sensor 66 of the end effector 46 is a pressure sensor or pressure measuring device, for example, a MEMS device. For a detailed description of various MEMS devices, reference may be made to U.S. Pat. No. 8,808,311, the entire contents of which are incorporated by reference herein. In embodiments, the second sensor 66 is disposed within the hollow inner chamber 60 of the inflatable member 56 and is configured to measure the amount of pressure applied by the end effector 46 to the grasped tissue (i.e., the clamping pressure) by measuring the pressure within the inflatable member 56. In addition to or in the alternative of inflatable member 56 having a pressure sensor, tissue contacting surface 48a of the staple cartridge 42a may also have a pressure sensor for measuring the amount of pressure applied by the end effector 46 to the grasped tissue.

The second sensor 66 (FIG. 3) is in electrical communication, via lead wires or wireless connection, with a second display section 20b (FIG. 1) of the display 20. After the second sensor 66 measures the clamping pressure applied to the grasped tissue, the second sensor 66 transmits the measurement data to the second display section 20b, which displays the measurement. Additionally or alternately, the second sensor 66 may send the measured clamping pressure to the computing device (e.g., a laser Doppler monitor) for processing, which then sends the information to the display 20.

The display 20 may have multiple display sections, for example, three display sections 20a, 20b, 20c. It is contemplated that the display 20 may include more or less than three discrete display sections arranged in any suitable configuration. In embodiments, the first display section 20a of the display 20 is configured to display a visual indication of a measured tissue perfusion of tissue grasped by the end effector 46. The second display section 20b of the display 20 is configured to display a visual indication of a measured amount of pressure being applied to tissue grasped by the end effector 46. A third display section 20c of the display 20 is configured to display an index representative of the ratio of the surface perfusion pressure determined using the first and second sensors 64, 66 of the surgical stapler 10, and a systemic blood pressure measured by a blood pressure cuff (not shown), as will be described in detail below.

In some embodiments, the display 20 (FIG. 1) may display ranges of numbers or various numeral outputs to display the measurements of first and second sensors 64, 66. In particular, the first, second, and third display sections 20a, 20b, 20c may display the number ranges 0 to 3, 0 to 5, 0 to 10, 0 to 100, or any other suitable range, to illustrate information about the tissue being grasped by the end effector 46. For example, when the first display section 20a displays the number 0, this may be an indication that the grasped tissue has very little or no perfusion (i.e., no blood flow), whereas when the first display section 20a displays the number 100, this may be an indication that the grasped tissue has a high perfusion (i.e., ideal blood flow).

In some embodiments, the display 20 may convey information about a characteristic of the grasped tissue utilizing any suitable indicia, for example, words such as poor, satisfactory, or good.

In some embodiments, the surgical system 1 may not include the display 20, and instead, surgical stapler 10 may be configured to be connected to or be in communication with another type of display, for example, a tablet, a cell phone, a computer monitor, a laptop, or any suitable display device. The surgical stapler 10 may be connected to any of the aforementioned display devices via USB wires, Wi-Fi, or the like.

In operation, the surgical system 1 may be used in a surgical procedure in which tissue is to be stapled, for example, an anastomotic surgical procedure, to gather various data about the subject tissue prior to effecting stapling. In some anastomotic surgical procedures, unhealthy or diseased bowel tissue is resected and the ends of the remaining healthy segments of bowel are stapled together to recreate a continuous bowel. Prior to stapling the ends of the separate bowel segments to one another, the viability of the ends of the separate bowel segments should be assessed in order to predict the likelihood of post-surgery anastomotic leaks or other adverse outcomes. To aid in making this viability assessment, a clinician may make use of the surgical system 1 of the present disclosure.

Figure 4:
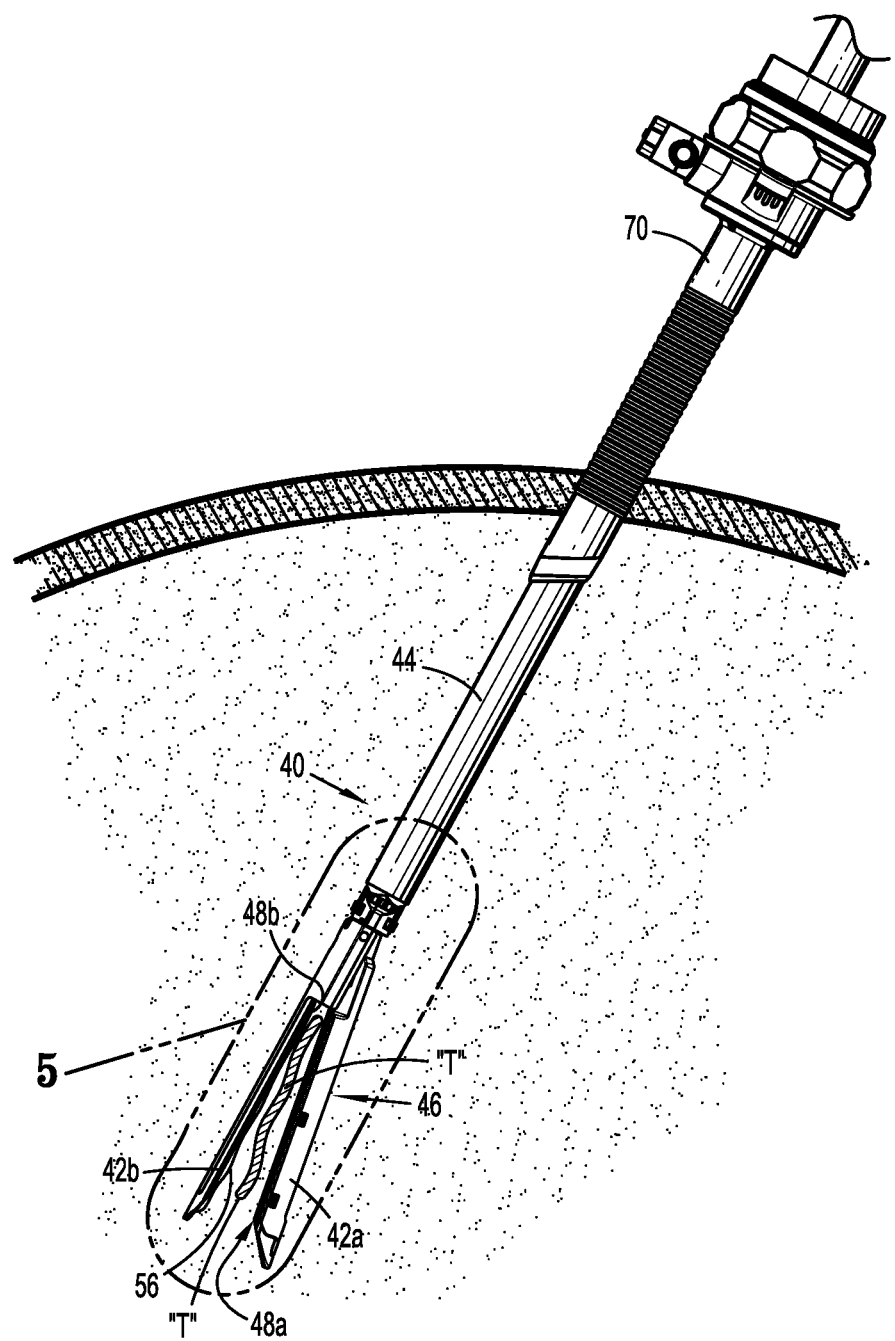
FIG. 4 is a side view of the surgical loading unit of FIG. 3 positioned at a surgical site via an access port.
Figure 7:
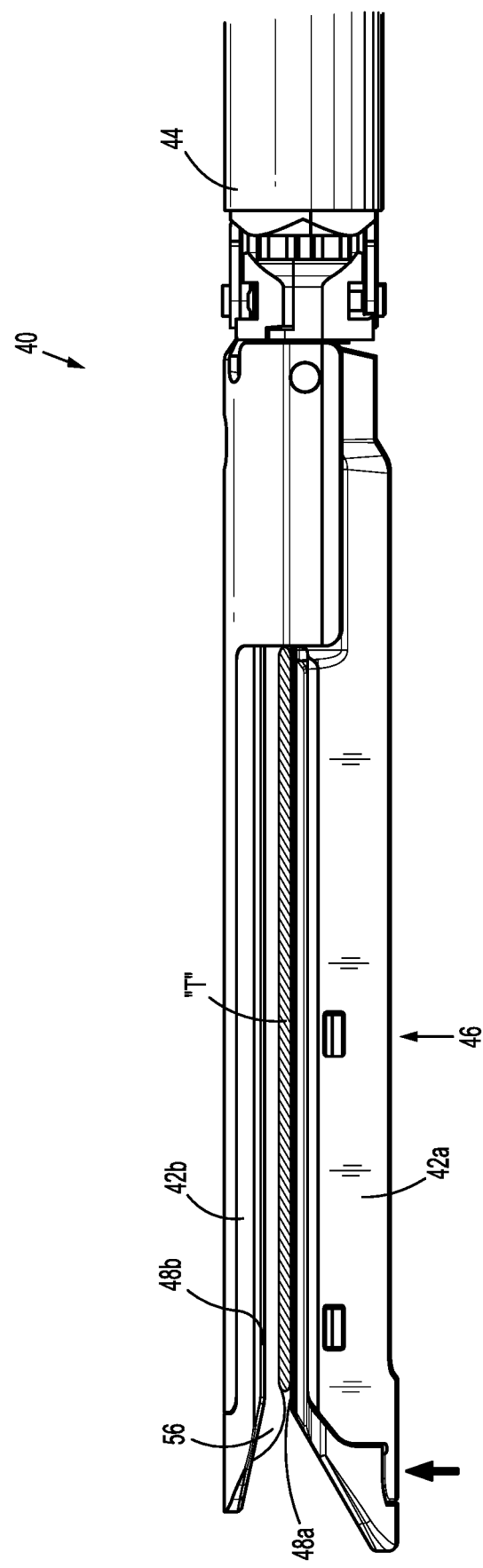
FIG. 7 is a partial, side view of the surgical loading unit of FIG. 3 illustrating the jaw members clamped about the tissue with the inflatable member in the expanded state.

With reference to FIG. 4, in use of the surgical system 1, the surgical loading unit 40 is positioned through an access port 70 to gain entry to a surgical site in a minimally invasive manner. With the inflatable member 56 of the end effector 46 in a collapsed or un-inflated state, tissue "T" is disposed between the tissue contacting surface 48a of the staple cartridge 42a and the inflatable member 56 disposed on the tissue-contacting surface 48b of the anvil 42b with the staple cartridge 42a and the anvil 42b in a partially open position, as shown in FIG. 5. With the tissue "T" disposed between the staple cartridge 42a and the anvil 42b, the pump of the surgical system 1 conveys a fluid (e.g., air) into the hollow inner chamber 60 of the inflatable member 56 via the tube 58 to change the inflatable member 56 from its collapsed state toward its expanded or inflated state, as shown in FIG. 6. With the inflatable member 56 in the expanded state, the staple cartridge 42a and the anvil 42b are clamped about the tissue "T," as shown in FIG. 7.

In one embodiment, the staple cartridge 42a and the anvil 42b may be clamped about the tissue "T" prior to expanding the inflatable member 56. As the pressure inside of the inflatable member 56 increases, the pressure applied to the tissue "T" disposed between staple cartridge 42a and the anvil 42b increases to inhibit blood flow through the tissue.

With the inflatable member 56 in the inflated state and the tissue "T" being grasped by the end effector 46, the first sensor 64 of the end effector 46 collects information about the perfusion through the grasped tissue. This information is transmitted to the first display section 20a of the display 20, which displays this information as an image of the blood flow or as a number representative of the degree of perfusion through the tissue "T." The second sensor 66 measures the pressure within the inflatable member 56 and sends this information to the second display section 20b of the display 20, which displays this information as a number. While a clinician monitors the perfusion reading (i.e., blood flow) displayed on the first display section 20a and the pressure reading displayed on the second display section 20b, expansion of the inflatable member 56 is gradually continued to gradually increase the clamping pressure between the staple cartridge 42a and the anvil 42b, until the perfusion reading indicates that no blood flow or virtually no blood flow is moving through the grasped tissue "T."

In embodiments, instead of gradually increasing the clamping pressure on the tissue "T" by inflating the inflatable member 56, the pivoting handle 16 is actuated to gradually close the staple cartridge 42a and the anvil 42b about the tissue "T." A clinician will cease approximating the staple cartridge 42a and the anvil 42b when the display section 20a indicates that no blood or virtually no blood is flowing through the tissue "T."

When the first display section 20a indicates that perfusion through the grasped tissue has ceased, a clinician continuously monitors both the first and second display sections 20a, 20b while the pump is activated to gradually withdraw the fluid from the inflatable member 56, decreasing the pressure applied to the grasped tissue "T." In embodiments, the pressured applied to the tissue "T" may be decreased by separating the staple cartridge 42a and the anvil 42b rather than by deflating the inflatable member 56. The clamping pressure is reduced until the first display section 20a displays a perfusion reading indicating that blood flow has returned to the grasped tissue. At the moment that the perfusion reading indicates that the blood flow is returned, the pressure reading (e.g., the pressure in inflatable member 56) displayed by the second display section 20b is noted, which is marks the local perfusion pressure of the grasped tissue.

The local perfusion pressure determined using the above-noted technique may be used to assess the viability of the grasped tissue by, for example, comparing the measured local perfusion pressure with a known local perfusion pressure associated with healthy or viable tissue. Additionally or alternately, the measured local perfusion pressure may be used in combination with other measurements, for example, a systemic blood pressure reading, to aid in making the determination of the viability of the tissue. The systemic blood pressure may be taken using any suitable device, for example, a blood pressure cuff, applied to any suitable body portion of the patient, for example, an arm of the patient. An index may be calculated by taking a ratio of the local perfusion pressure measured by the surgical stapler 10 and the systemic blood pressure taken using the blood pressure cuff. The index may be calculated by the computing device in the display 20 and displayed as a number on the third display section 20c of the display 20.

The calculated index is predictive of whether an anastomotic leak may occur and/or the grade of an anastomotic leak. As such, a clinician can use the index to make a determination on whether the two ends of the presumed healthy bowel segments are healthy enough to be stapled together or whether more tissue needs to be resected. For example, the calculated index may be compared to a known index that is associated with healthy tissue. For a detailed description of a method of calculating a perfusion index and using the calculated index to assess tissue viability, reference may be made to U.S. Pat. No. 7,618,376, the entire contents of which were incorporated by reference above.

After determining that the grasped tissue "T" is viable, the movable handle 18 of the surgical stapler 10 may be actuated to eject staples from the staple-receiving channels 50 of the staple cartridge 42a into the tissue "T." The staples contact the staple-forming pockets 52 of the anvil 42b to close the staples about the tissue "T." As the staples are ejected, a cutting blade (not shown) moves through the end effector 46 to cut the stapled tissue "T," thereby dividing the tissue "T" into two tissue segments.

In this way, a clinician only needs to use one instrument, namely the surgical stapler 10 of the present disclosure, to both determine tissue viability and to effect a stapling procedure once it is determined that the tissue is viable. One benefit to having only one instrument to accomplish each of these tasks is that once the surgical instrument determines that a particular segment of tissue is viable, the clinician can immediately staple the tissue without having to use a separate surgical stapler.

In some embodiments, the surgical stapler 10 may be pre-programmed to inflate the inflatable member 56 to exert a predetermined clamping pressure that is known to result in a ceasing of perfusion through the grasped tissue. The surgical stapler 10 may also be pre-programmed to reduce the clamping pressure at a predetermined rate via deflation of the inflatable member 56 and automatically send the pressure reading to the computing device at the moment when perfusion through the grasped tissue restarts. The perfusion pressure reading may also be displayed on the display 20. This automated process eliminates human error in operating the surgical stapler 10 by controlling the amount of clamping pressure being applied to the tissue at any given time instead of the clinician.

In addition to the surgical system 1 being used to ensure that the tissue is in condition for stapling or acceptable for stapling, the surgical system 1 may also be used as a check after the staples have been fired to ensure that the tissue is healthy (e.g., has good blood flow, is healing properly, etc.).

The surgical system 1 or components thereof may be configured to be incorporated into a robotic surgical system (not shown). The robotic surgical system is powered locally or remotely, and has electronic control systems localized in a console or distributed within or throughout the robotic surgical system. The robotic surgical system permits a clinician to remotely manipulate the surgical stapler 10 to more precisely control the movement of the surgical stapler 10. The surgical stapler 10 may be configured to send the measurements gathered by the sensors 64, 66 of the end effector 46 to an interface of the robotic surgical system on which the measurements may be displayed for the clinician to read. In any of the embodiments disclosed herein, the surgical instrument can be a surgical stapler other than a linear endoscopic surgical stapler. For example, a circular stapler can incorporate a perfusion system disclosed herein.

Figure 8:
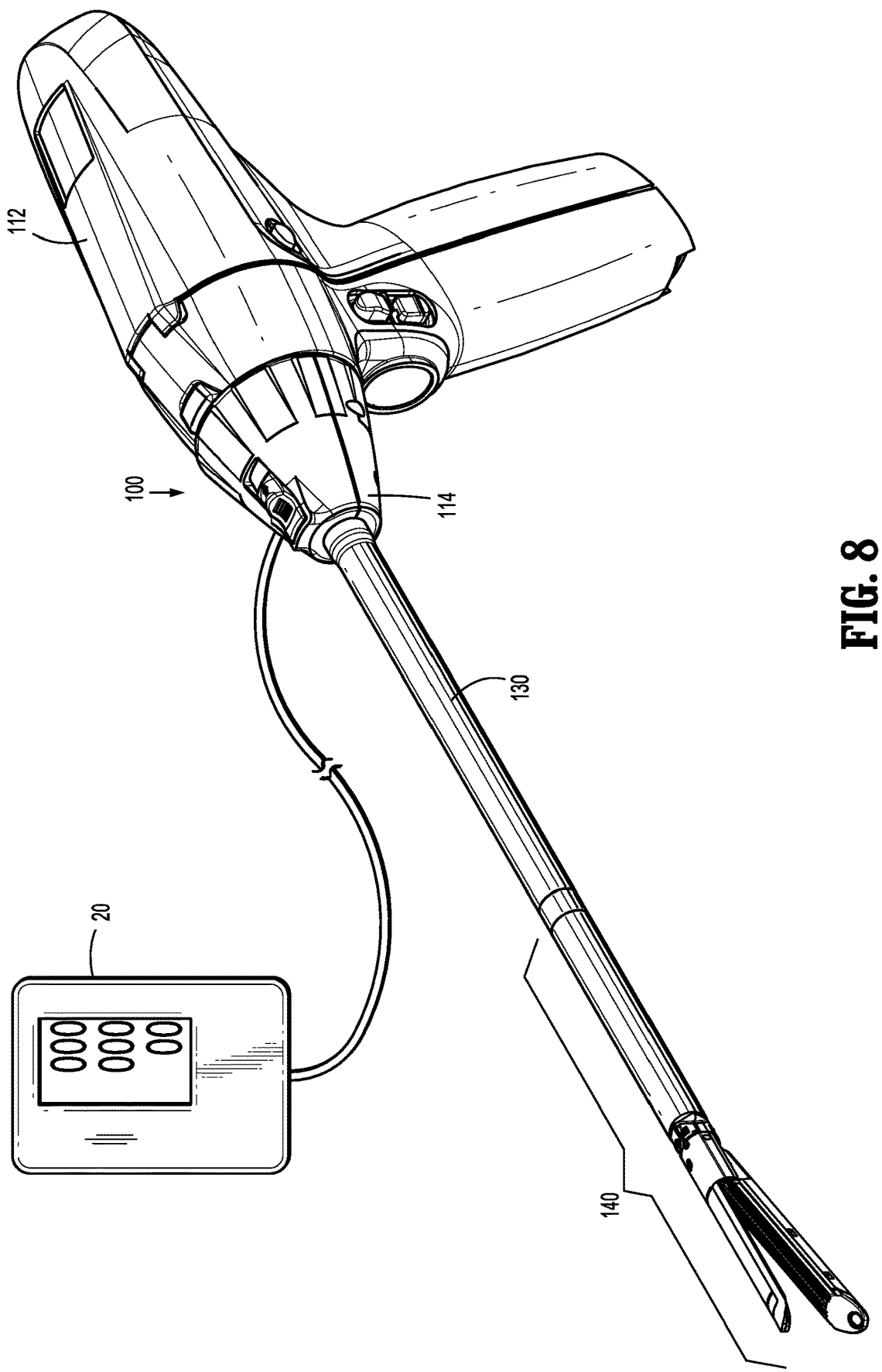
FIG. 8 is a perspective view of another embodiment of a surgical system including a display and a surgical instrument including the surgical loading unit of FIG. 3.

As illustrated in FIG. 8, another embodiment of a surgical instrument 100 for use with the display 20 is provided. The surgical instrument 100 is similar to surgical stapler 10 described with reference to FIGS. 1-7, and will therefore only be described with the detail necessary to elucidate differences.

Surgical instrument 100 is a surgical stapler configured to both staple tissue and to determine tissue viability using an inflatable member (not explicitly shown), a perfusion sensor (not explicitly shown), and a pressure sensor (not explicitly shown). As described above in regard to the surgical stapler 10, the surgical instrument 100 includes a handle portion 112, an adapter assembly 114, an elongated shaft 130, and a surgical loading unit 140. However, rather than being manually-powered as is the surgical stapler 10 of FIGS. 1-7, the surgical instrument 100 of the present embodiment actuates functions of the surgical loading unit 140 (e.g., stapling, cutting, closing/opening of the jaws, etc.) via an internal-power source disposed within the handle portion 112. For a detailed description of an exemplary internally-powered handle portion of a surgical stapler, reference may be made to U.S. Patent Application Publication No. 2016/0118201, filed on Jul. 24, 2015, the entire contents of which being incorporated by reference herein.

Figure 9:
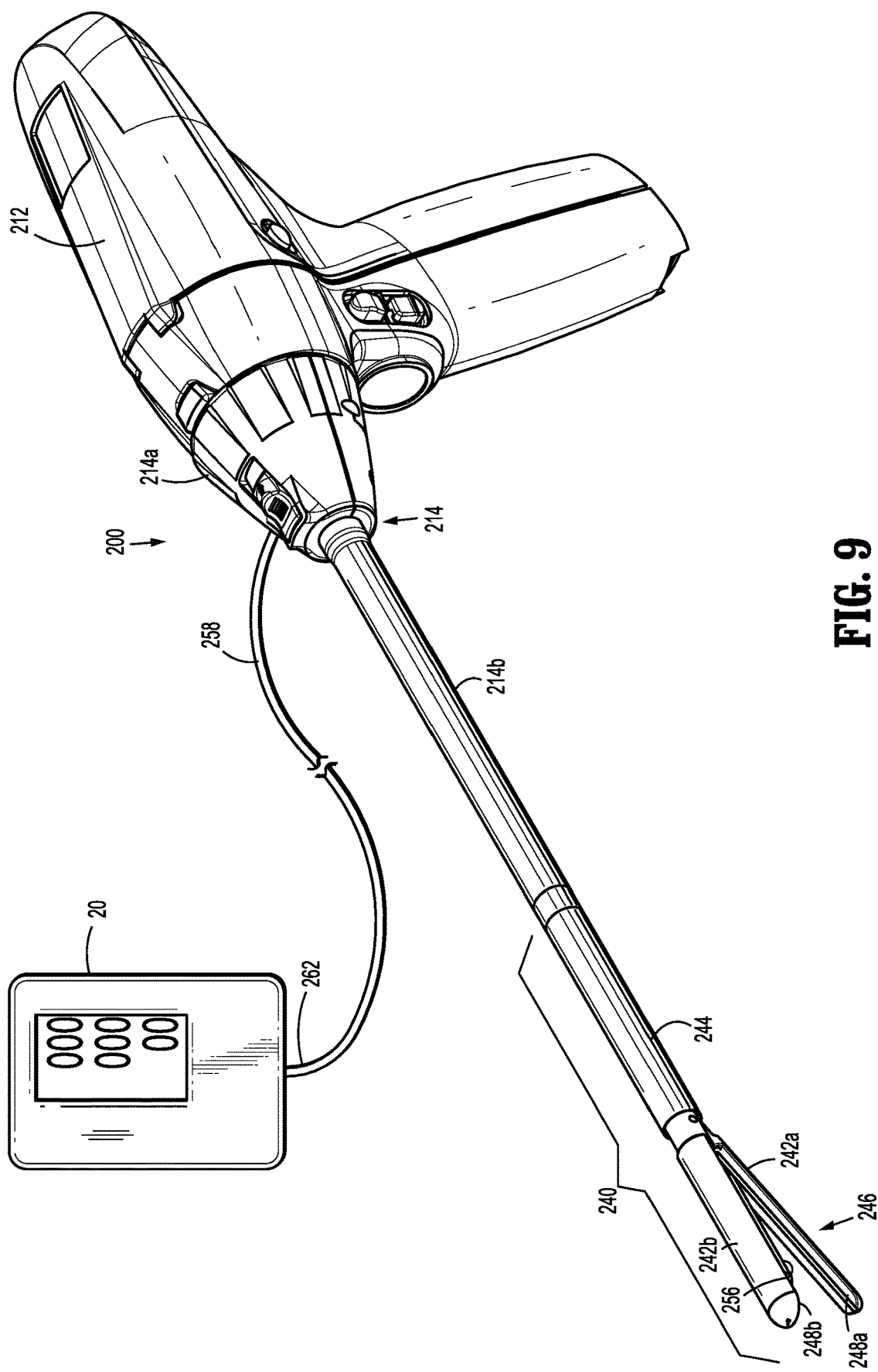
FIG. 9 is yet another embodiment of a surgical system including a display and a surgical instrument.
Figure 10:
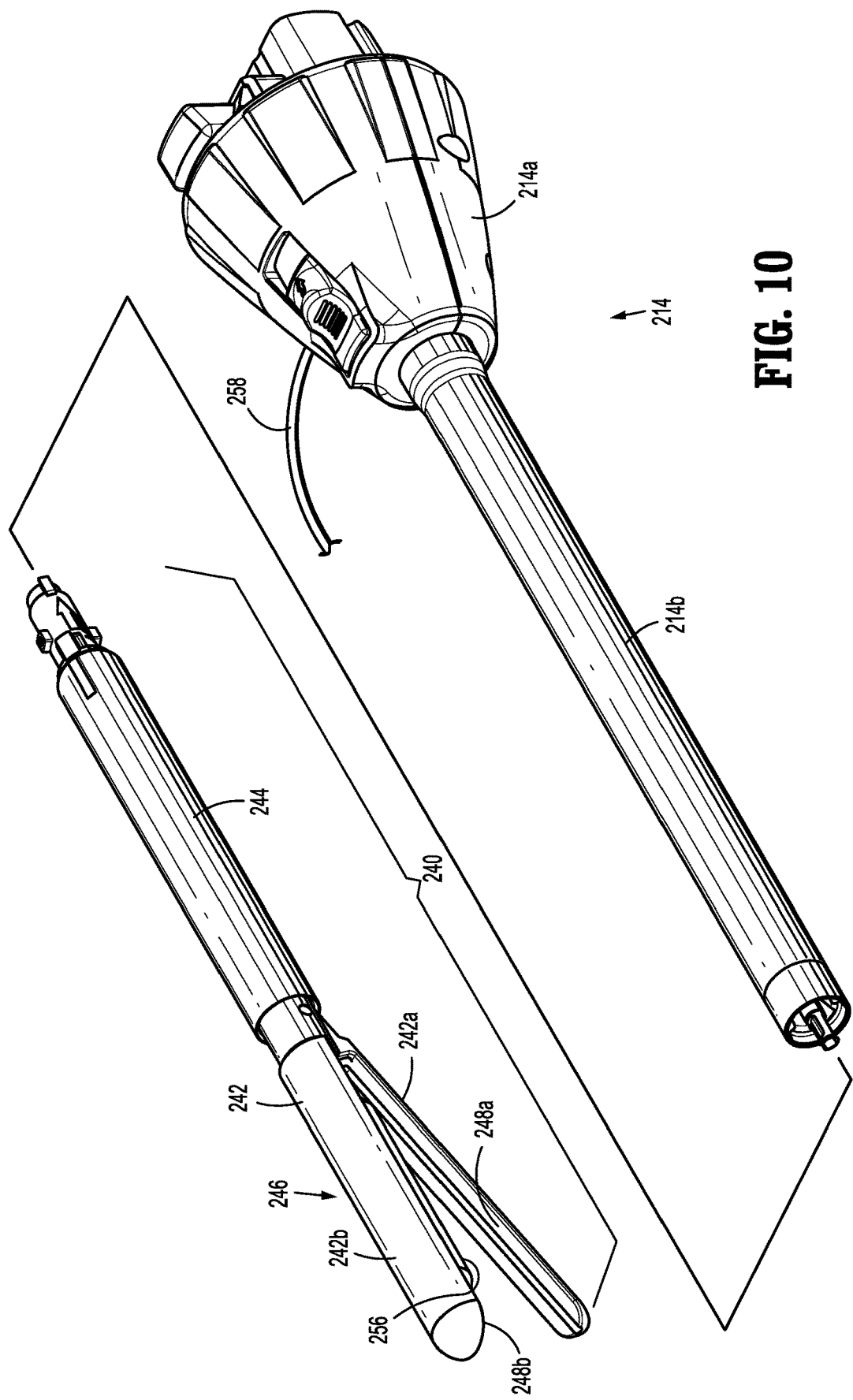
FIG. 10 is a perspective view, with parts separated, of a surgical loading unit and an adapter assembly of the surgical instrument of FIG. 9.
Figure 11:
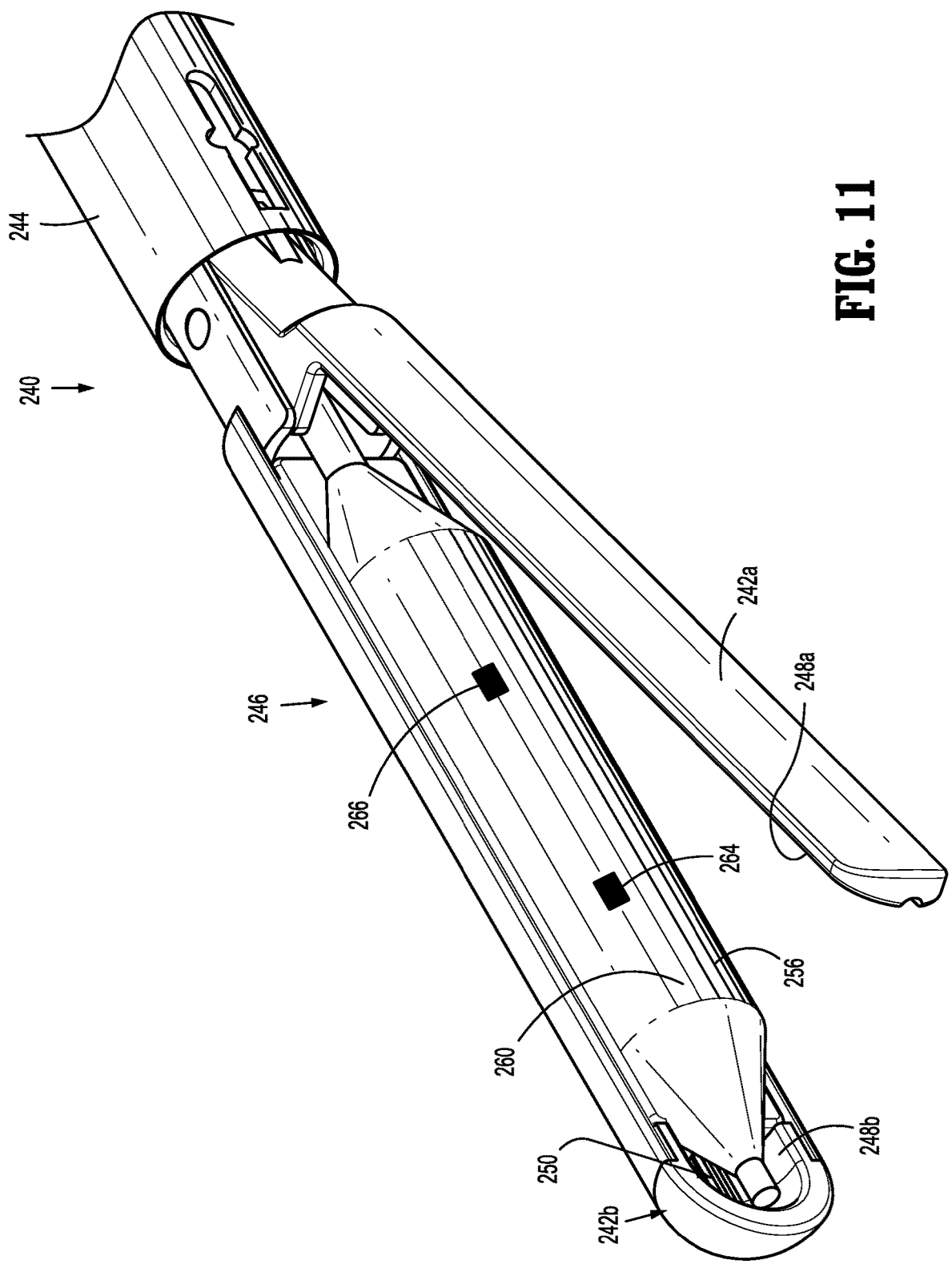
FIG. 11 is an enlarged, perspective view of the surgical loading unit of FIG. 10.

As illustrated in FIGS. 9-11, another embodiment of a surgical instrument 200 for use with the display 20 is provided. The surgical instrument 200 is similar to the surgical stapler 10 described with reference to FIGS. 1-7, and will therefore only be described with the detail necessary to elucidate differences.

Surgical instrument 200 is a non-stapling tissue grasper configured to determine tissue viability of grasped tissue. The tissue grasper 200 includes a handle portion 212, an adapter assembly 214, and a surgical loading unit 240. The adapter assembly 214 includes a housing or knob 214a and an elongated shaft 214b extending distally therefrom. The knob 214a of the adapter assembly 214 is configured to detachably couple to the handle portion 212.

The surgical loading unit 240 has an elongated body portion 244 and a jaw assembly 246 coupled to the body portion 244. The body portion 244 is detachably coupled to a distal portion of the elongated shaft 214b of the adapter assembly 214. The jaw assembly 246 includes a first jaw 242a and a second jaw 242b each coupled to the distal portion of the body portion 244. The first jaw 242a is pivotably coupled to the body portion 244 such that the first jaw member 242a is movable relative to the second jaw member 242b between a spaced condition and an approximated condition. In some embodiments, one or both of the jaw members 242a, 242b may be pivotably coupled to the body portion 244 of the surgical loading unit 240.

The first jaw member 242a has a tissue-contacting surface 248a and the second jaw member 242b has an inner surface 248b that defines an elongated cavity 250 (FIG. 11) therein. The jaw assembly 246 includes an inflatable member 256, similar to inflatable member 56 described above, received within the cavity 250 of the second jaw member 242b. The inflatable member 256 may be dimensioned for a snap-fit engagement with the inner surface 248b of the second jaw member 242b. The inflatable member 256 has a generally rectangular shape dimensioned to contact the tissue-contacting surface 248a of the first jaw member 242a when the jaw assembly 244 is in the approximated state.

The inflatable member 256 is configured to be changed or moved from a collapsed configuration, in which the inflatable member 256 is substantially flat and rectangular, to an expanded configuration, in which the inflatable member 256 is larger than in the collapsed configuration and assumes a bulbous configuration. The inflatable member 256 may have a hose or tube 258 (FIG. 9) extending therefrom and in fluid communication with a hollow inner chamber 260 defined in the inflatable member 256. The tube 258 may have an end 262 coupled to a source of fluid, such as, for example, a pump (not explicitly shown), for delivering a fluid such as liquid and/or gas into hollow inner chamber 260 of the inflatable member 256.

The jaw assembly 140 includes a perfusion sensor 264 (FIG. 11), similar to the first sensor 64 described above, and a pressure sensor 266, similar to the second sensor 66 described above. The perfusion sensor 264 is attached to the inflatable member 256 (e.g., an inner or outer surface thereof) of the second jaw member 242b and in communication with the display 20. In some embodiments, the perfusion sensor 264 may be attached to the tissue-contacting surface 248a of the first jaw ember 242a or the inner surface 248b of the second jaw member 242b rather than the inflatable member 256.

In embodiments, the pressure sensor 266 (FIG. 11) of the jaw assembly 246 is disposed within the hollow inner chamber 260 of the inflatable member 256 and is configured to measure the amount of pressure applied by the jaw assembly 246 to the grasped tissue (i.e., the clamping pressure) by measuring the pressure within the inflatable member 256. In addition to or in the alternative of inflatable member 256 having a pressure sensor, the tissue contacting surface 248a of the first jaw member 242a may also have a pressure sensor for measuring the amount of pressure applied by the jaw assembly 246 to the grasped tissue.

The tissue grasper 200 is used in a similar manner as described above with respect to the surgical stapler 10 except that the tissue grasper 200 does not effect a stapling of the grasped tissue after the viability of the grasped tissue is assessed.

Figure 12:
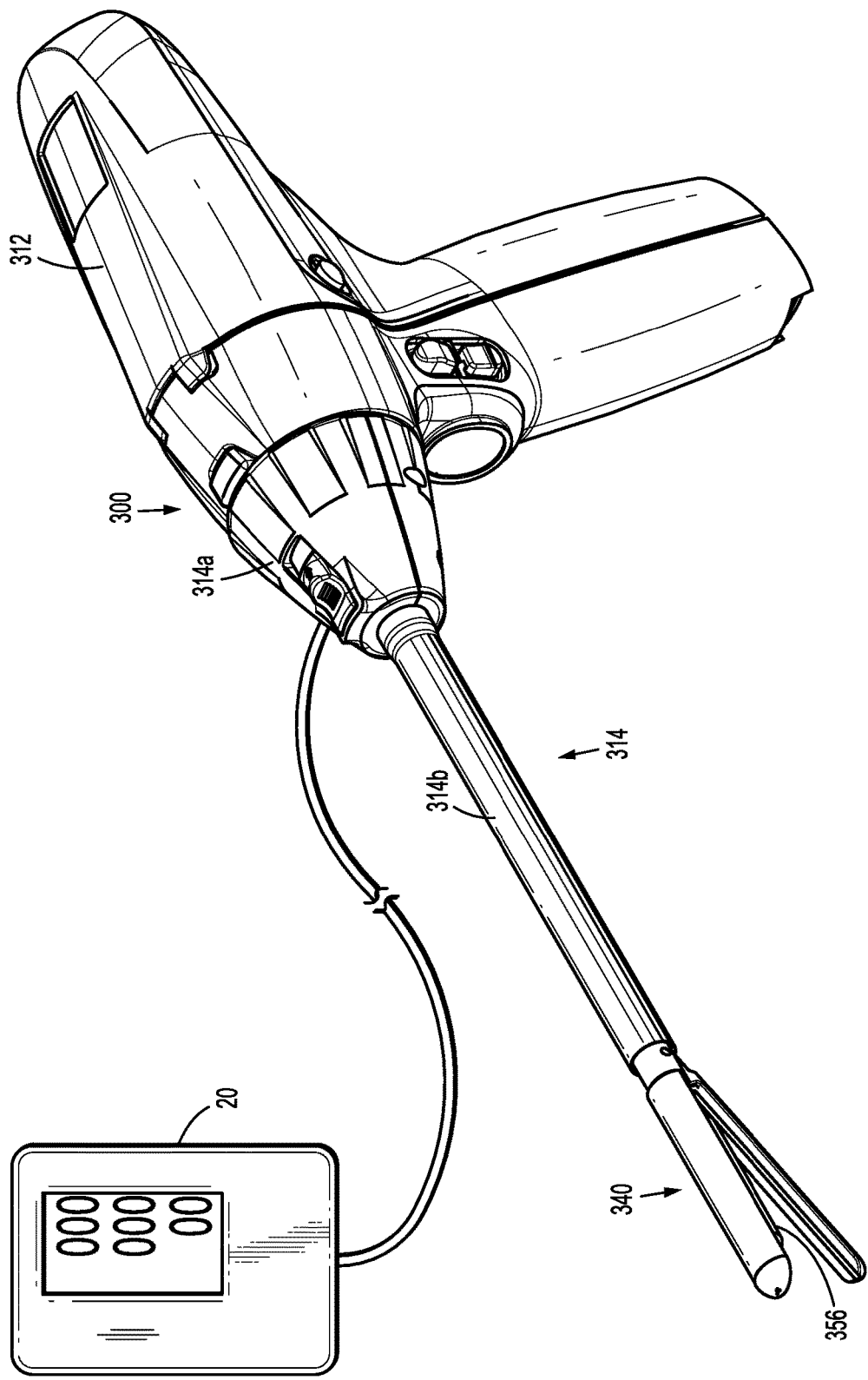
FIG. 12 is yet another embodiment of a surgical system including a display and a surgical instrument.

As illustrated in FIGS. 12 and 13, another embodiment of a surgical instrument 300 for use with the display 20 is provided. The surgical instrument 300 is similar to the surgical instrument 200 described above with reference to FIGS. 9-11, and will therefore only be described with the detail necessary to elucidate differences.

The surgical instrument 300 is a tissue grasper configured to grasp tissue and determine viability of the grasped tissue using an inflatable member 256, a perfusion sensor (not explicitly shown), and a pressure sensor (not explicitly shown). The tissue grasper 300 includes a handle portion 312, an adapter assembly 314, and a jaw assembly 340. Rather than the tissue grasper 300 having a detachable loading unit, the jaw assembly 340 is fixed to the elongated shaft 314b of the adapter assembly 314, and a housing or knob 314a of the adapter assembly 314 is detachably coupled to the handle portion 312.

Although the illustrative embodiments of the present disclosure have been described herein, it is understood that the disclosure is not limited to those precise embodiments, and that various other changes and modifications may be affected therein by one skilled in the art without departing from the scope or spirit of the disclosure. All such changes and modifications are intended to be included within the scope of the disclosure.

What is claimed is:

1. A surgical instrument, comprising:
a handle portion;
a shaft coupled to the handle portion;
a pair of jaw members operably coupled to the shaft and movable relative to one another between spaced and approximated positions in response to an actuation of the handle portion, the pair of jaw members configured to perform a stapling function;
an inflatable member detachably connected to a first tissue-contacting surface of a first jaw member of the pair of jaw members via a fastener such that upon an actuation of the stapling function of the pair of jaw members, the inflatable member is configured to release from the first tissue-contacting surface by the stapling function severing the fastener, the inflatable member configured to apply pressure to tissue disposed between the pair of jaw members;
a first sensor associated with the at least one of the pair of jaw members, the first sensor being configured to measure local perfusion in the tissue disposed between the pair of jaw members; and
a second sensor in communication with the inflatable member and configured to measure a pressure within the inflatable member, wherein the surgical instrument is configured to indicate a local perfusion pressure of the tissue using the first and second sensors.

2. The surgical instrument according to claim 1, wherein the first tissue-contacting surface defines staple-forming pockets and a second jaw member of the pair of jaw members includes a second tissue-contacting surface that defines staple-receiving channels.

3. The surgical instrument according to claim 1, wherein the inflatable member is a balloon fabricated from a biocompatible elastomer.

4. The surgical instrument according to claim 1, wherein the inflatable member has a tube configured to be in fluid communication with a pump for inflating the inflatable member.

5. The surgical instrument according to claim 1, wherein the inflatable member is configured to transition between a collapsed state, in which the inflatable member is flat, and an expanded state, in which the inflatable member is bulbous.

6. The surgical instrument according to claim 1, wherein the inflatable member defines a hollow inner chamber therein.

7. The surgical instrument according to claim 1, wherein the handle portion includes a manual trigger for effecting a closing of the pair of jaw members.

8. The surgical instrument according to claim 1, wherein the handle portion is configured to effect a closing of the pair of jaw members via an internal power source.

9. The surgical instrument according to claim 1, further comprising an adapter assembly interposed between the handle portion and the shaft.

10. A surgical instrument, comprising:
a handle portion;
a shaft coupled to the handle portion;
a pair of jaw members operably coupled to the shaft and movable relative to one another between spaced and approximated positions in response to an actuation of the handle portion, the pair of jaw members configured to perform a stapling function and including a first jaw member having a first tissue-contacting surface and a second jaw member having a second tissue-contacting surface;
an inflatable member having an elongated configuration and spanning a majority of a length of the first jaw member of the pair of jaw members, the inflatable member being detachably connected to the first tissue-contacting surface of the first jaw member via a suture such that upon an actuation of the stapling function of the pair of jaw members, the inflatable member is configured to release from the first tissue-contacting surface by the stapling function severing the suture, the inflatable member being configured to apply pressure to tissue disposed between the pair of jaw members; and
a first sensor associated with at least one of the first or second jaw members of the pair of jaw members, the first sensor configured to measure local perfusion in the tissue disposed between the pair of jaw members.

11. The surgical instrument according to claim 10, further comprising a second sensor in communication with the inflatable member and configured to measure a pressure within the inflatable member, wherein the surgical instrument is configured to indicate a local perfusion pressure of the tissue using the first and second sensors.

12. The surgical instrument according to claim 10, wherein the inflatable member covers a majority of the first tissue-contacting surface.

13. The surgical instrument according to claim 10, wherein the inflatable member has a tube configured to be in fluid communication with a pump for inflating the inflatable member.

14. The surgical instrument according to claim 10, wherein the inflatable member is configured to transition between a collapsed state, in which the inflatable member is flat, and an expanded state, in which the inflatable member is bulbous.

* * * * *